July 19, 1927. O. H. OESTERWITZ Re. 16,687
SURGICAL INSTRUMENT
Original Filed Feb. 21, 1922.
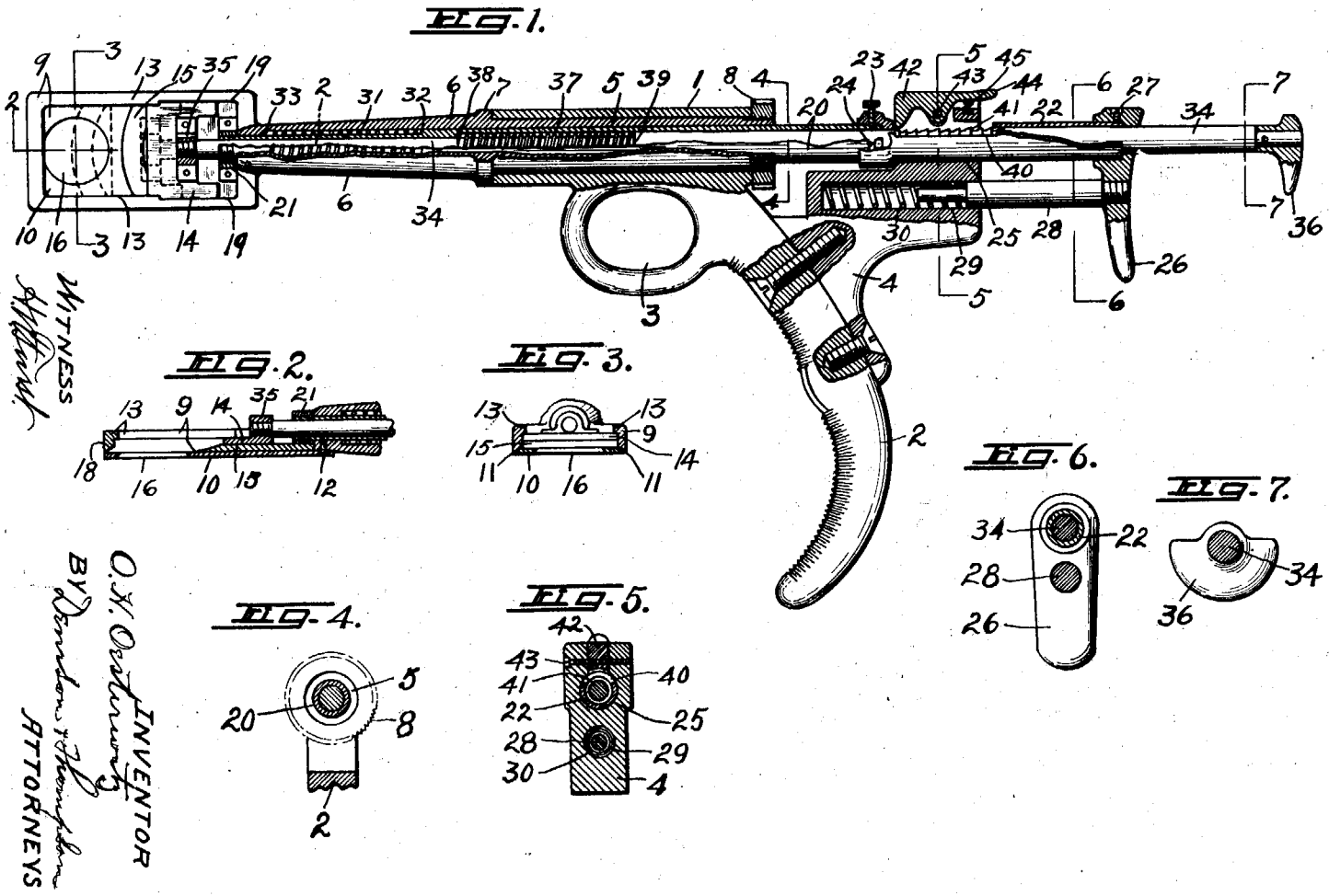

Reissued July 19, 1927. Re. 16,687

UNITED STATES PATENT OFFICE.

OTTO H. OESTERWITZ, OF SYRACUSE, NEW YORK.

SURGICAL INSTRUMENT.

Original No. 1,448,858, dated March 20, 1923, Serial No. 538,184, filed February 21, 1922. Application for reissue filed March 3, 1925. Serial No. 13,006.

This invention relates to a surgical instrument for removing infected tonsils and analogous operations in which an apertured spatula adapted to receive the infected part is mounted upon a suitable handle to co-operate with holding and cutting blades which are relatively slidable upon the spatula to and from a position across the opening therein for holding and severing the infected part and are adapted to be operated independently of each other by reciprocatory plungers on the handle.

The main object is to provide a simple instrument of this character which may be held steadily in the hand and directed to the work with greater expedition and accuracy than has heretofore been practiced and at the same time to enable the severed infected part to be positively removed without liability of contaminating other parts.

Another object is to enable the infected part to be compressed in advance of and during the cutting operation to assure a complete removal thereof.

Other objects and uses relating to specific parts of the device will be brought out in the following description.

In the drawings:

Figure 1 is a side elevation partly in section of a surgical instrument embodying the various features of my invention.

Figure 2 is a detail longitudinal sectional view taken on line 2—2, Figure 1.

Figures 3, 4, 5, 6 and 7 are transverse detail sectional views taken, respectively, on lines 3—3, 4—4, 5—5, 6—6 and 7—7, Figure 1.

As illustrated, this device comprises a tubular head or barrel —1— having a handle —2— by which the entire device may be supported in one hand, said handle being provided with a finger opening —3— for the reception of the fore-finger to facilitate the holding and directing of the device to the work, the barrel —1— serving to receive certain movable parts hereinafter described.

A bracket —4— is secured to and extends upwardly and rearwardly from the handle —2— to receive other movable parts and together with the barrel and handle constitute the main frame of the instrument.

The barrel —1— is provided with a lengthwise cylindrical bore for receiving a cylindrical portion —5— of a tubular sleeve —6— which is rotatably mounted in the barrel to turn about its axis and extends therethrough and some distance beyond the opposite ends thereof, said sleeve being provided with annular shoulders —7— and —8— engaging opposite ends of the barrel for holding the sleeve against relative endwise movement, one of said shoulders as —8— consisting of a knurled nut engaging an adjacent threaded end of the sleeve for clamping the same in any position of rotary adjustment in addition to its function of holding the sleeve against forward displacement.

The forward end of the sleeve —6— is provided with a substantially flat rectangular head —9— elongated longitudinally and mainly in a plane below the axis of the sleeve to form what may be termed "a spatula" and consisting of an open frame having a hardened steel shearing blade —10— across one face thereof, said frame being provided with dovetailed ribs —11— along its marginal edges for receiving said blade, which is also provided with dove-tailed edges for engaging the dove-tailed ribs by lengthwise sliding movement and thereby aiding in holding the blade and frame in operative position, the blade being additionally secured at its rear end to the frame by a screw —12— to hold it against endwise movement in the ways —11— when the parts are adjusted for use.

The opposite side and front end of the frame is provided with inwardly projecting flanges —13— to form guides for a holding blade —14— and a cutting blade —15—, both of which are slidable lengthwise of and within the frame —9— between the guide flanges —13— and shearing plate —10— and from a position across an opening —16— in said plate. This opening —16— is preferably circular for receiving the infected parts to be severed and its edges are preferably knife-shaped to cooperate with the blade —15— in severing the infected part.

That is, the opening —16— is formed in the forward portion of the plate —10— just back of the front edge thereof, while the blade —15— is moved flatwise along and against the inner face of the plate —10— and is provided with a convex forward cutting edge for cooperation with the cutting edge around the opening —16— in the blade —10— as the blade —15— is moved from a normal position at the rear of the opening to a position across said opening, the front end of the frame being beveled at —18— to receive the cutting edge of the blade —15— and thereby to assure its complete movement across the opening.

The holding blade —14— is slidable lengthwise of and upon the cutting blade —15— to and from a position across the opening —16— for compressing the infected part and holding the same during the cutting operation by the blade —15—, the combined thicknesses of the blades —14— and —15— being substantially equal to the space between the inner faces of the plate —10— and flanges —13—, which latter overlie the adjacent longitudinal edges of the blade —14— to hold said blades in close juxtaposition to each other and to assure a close shearing cooperation between the blade —15— and plate —10—.

The rear ends of the lengthwise flanges —13— are cut away at —19— a distance slightly greater than the length of the plate —14— to allow the latter to be removed when disconnected from its operating mechanism hereinafter described, the plate —10— being also removable for resharpening if desired by simply removing the clamping screw —12— and withdrawing the plate forwardly from the frame.

A tubular stem or plunger —20— is slidable lengthwise of and within the sleeve —6— and extends beyond the opposite ends thereof, the forward end being threaded and secured in an internally threaded boss —21— on the rear end of the knife blade —15—, the rear end being detachably coupled to a coaxial tubular section —22— by means of a set screw —23—, which is engaged in a radial threaded aperture in the adjacent end of the tubular section —22— and projected into an annular groove —24— in the adjacent end of the section —20— to permit rotation of the section —20— relatively to the section —22— as the tubular sleeve with the spatula —9— thereon is turned about its axis to properly adjust the spatula to the infected part to be removed.

The tubular section —22— is slidable lengthwise of and within a guide opening —25— in the bracket —4—, the portion of the bracket in which the guide opening —25— is formed being spaced longitudinally from the rear end of the sleeve —6— a distance somewhat greater than the distance of travel of the cutting blade —15— in the frame —9— to allow the sections —20— and —22— to move a sufficient distance to effect the opening and closing movement of the cutting blade.

The forward end of the tubular section —22— is preferably enlarged to receive the adjacent end of the section —20— and forms a stop shoulder adapted to engage the adjacent end of the bracket —4— for limiting the rearward or opening movement of the blade and its actuating sleeves —20— and —22—. The rear end of the sleeve section —22— extends some distance beyond the corresponding end of the bracket —4— and is provided with an operating handle —26— secured thereto by a set screw —27— and extending downwardly therefrom a sufficient distance to receive and support a guide rod —28— which is movable in a guide socket —29— in the bracket —4— parallel with the axis of the barrel —1—.

A coil spring —30— is arranged in the socket —29— for engaging and retracting the guide rod —28— and also for retracting the tubular sections —20— and —22— through the medium of the handle —26— and coupling screw —23—.

The front end of the sleeve section —20— is reduced in diameter to receive a coil spring —31— which is interposed between said reduced portion and the inner bore of the sleeve —6— and has one end abutting against a shoulder —32— on the section —20— and its other end abutting against a shoulder —33— on the front end of the sleeve —6— to assist in retracting the sections —20— and —22— by direct axial pressure.

A plunger rod —34— extends entirely through the tubular sections —22— and —20— and has its forward end threaded and engaged with an internally threaded boss —35— on the holding plate —14— while the rear end extends some distance beyond the handle —26— and is provided with a separate handle —36— for moving it independently of the sleeves —20— and —22— against the action of a retracting spring —37—, which encircles a reduced portion of the rod —34— within the sleeve section —20— and has one end engaged with a shoulder —38— on said sleeve and its other end engaged with a similar shoulder —39— on the rod. These coil springs —31— and —37— are arranged wholly within the tubular sleeve —6— between the opposite ends thereof but are spaced apart coaxially.

The portion of the tubular section —22—, which extends through the bracket —4— is provided in its upper side with a lengthwise slot —40— for exposing the adjacent portion of the plunger rod —34— which is provided with teeth or serrations —41— registering through the slot and adapted to be engaged by the forward end of a detent —42—, the latter being pivoted intermediate its ends at —43— to the bracket —4— directly over the rod —34— and tubular section —22— and has its rear end constituting a finger piece —44— which may be depressed to release the detent against the action of a retracting spring —45—.

*Operation.*

Assuming that the various movable parts are in their normal position and that it is desired to remove an infected tonsil, the instrument is held by the handle —2— in position to insert the spatula —9— in the mouth of the patient so that the infected part may be caused to pass through the opening —16—, whereupon the rod —34— may be gradually advanced by the other hand through the medium of the handle —36— until the infected part is gripped and held between the jaw —14— and forward end of the spatula where it is held by the engagement of the pawl —42— with the teeth —41— after which the tubular plunger sections —20— and —22— may be similarly advanced by means of the handle —26— independently of the rod —34— to cause the knife blade —15— to coact with the shearing edges of the plate —10— to sever the infected part, while it is still held by the jaw —14—, thus permitting the instrument to be withdrawn from the mouth with the infected part therein.

The detent —42— is then tripped by means of the finger piece —44— to allow the rod —34— and plunger sections —20— and —22— together with the holding jaw —14— and blade —15— to be returned to their normal positions by means of the retracting springs —30—, —31— and —37— ready for other similar operations, it being understood that the severed infected part is properly disposed of.

The angular adjustment of the head or plate —9— and its supporting sleeve —6— in the barrel —1— permit the instrument to be used in operating upon different parts of the mouth or at different angles relatively to the plane of the handle —2— which may always be held in an upright position, this angular adjustment being also transmitted to the tubular section —20— and rod —34— relatively to the tubular section —22— through the medium of the turning joint at the coupling screw —23—.

The teeth —41— form annular shoulders on the rod —34—, the latter to be unscrewed from the boss —35— of the holding jaw —14— which permits said rod to be withdrawn rearwardly from the tubes —20— and —22— by simply releasing the detent —42—, thus permitting the jaw —14— to be removed when registered with the cutaway portions —19— of the guide flanges —13— for cleansing and sterilizing purposes.

When the rod —34— is unscrewed from the boss —35—, the sleeve —6— and tubular section —20— may be withdrawn forwardly from the barrel —1— by simply unscrewing the nut —8— and loosening the coupling screw —23—, whereupon the tubular section —20— may be unscrewed from the boss —21— on the cutting blade —15— and withdrawn rearwardly from the sleeve —6—, thus permitting the removal of the blade —15— for cleansing and sterilizing and allowing the spatula and shearing plate —10— to be similarly cleansed and sterilized, it being understood that the plate —10— may also be withdrawn from the frame —9— by simply loosening the screw —12—.

What I claim is:—

1. In a surgical instrument of the character described, the combination of a frame, a tubular sleeve mounted thereon, a spatula secured to the sleeve and provided with an opening having a shearing edge, a cutter reciprocally movable on the spatula to and from a position across the opening and cooperating with said cutting edge, a jaw reciprocally movable on the spatula to and from a position across the opening, and separate devices for reciprocating the cutter and jaw independently of each other.

2. In a surgical instrument of the character described, the combination of a frame, a tubular sleeve mounted thereon, a spatula secured to the sleeve and provided with an opening having a shearing edge, a cutter reciprocally movable on the spatula to and from a position across the opening and cooperating with said cutting edge, a jaw reciprocally movable on the spatula to and from a position across the opening, separate devices for reciprocating the cutter and jaw independently of each other, and means for holding the jaw-operating means in different positions of adjustment.

3. In a surgical instrument of the character described, the combination of a tubular sleeve having a relatively fixed jaw, a tubular plunger reciprocally movable endwise through the sleeve and provided with a cutter cooperating with the fixed jaw to sever the part to be removed, and a rod reciprocally movable endwise through the tubular plunger and provided with a jaw cooperating with the fixed jaw to hold said part while being severed by the cutter.

4. In a surgical instrument of the character described, the combination of a barrel having a handle, a sleeve mounted in the barrel and provided with a relatively fixed jaw, a tubular plunger reciprocally movable in the sleeve and provided with a cutting blade movable therewith toward and from the fixed jaw, a rod reciprocally movable in the tubular plunger and provided with a jaw movable toward and from the fixed jaw as the rod is reciprocated, and a detent for holding the rod in different positions of adjustment.

5. In a surgical instrument of the character described, the combination of a barrel having a handle, a sleeve mounted in the barrel and provided with a relatively fixed jaw, a tubular plunger reciprocally movable in the sleeve and provided with a cutting blade movable therewith toward and from the fixed jaw, a rod reciprocally movable in the tubular plunger and provided with a jaw movable toward and from the fixed jaw as the rod is reciprocated, and a detent for holding the rod in different positions of adjustment, said sleeve being adjustable rotarily in the barrel.

6. In a surgical instrument of the character described, the combination of a barrel having a handle, a sleeve journaled in the barrel for relative rotary adjustment and provided with shoulders engaging opposite ends of the barrel to hold it against relative endwise movement, one of said shoulders being removable to permit endwise displacement of the sleeve from the barrel, a relatively fixed shoulder on the sleeve, a tubular plunger reciprocally movable lengthwise of and within the sleeve and provided with a knife-blade movable toward and from the fixed shoulder as the plunger is reciprocated, a handle on the plunger for moving it in one direction, a retracting spring for the plunger, a rod reciprocally movable lengthwise of and within the plunger and provided with a jaw movable toward and from the fixed jaw as the rod is reciprocated, a handle on the rod for moving it in one direction, a retracting spring for said rod, and a detent for holding the rod in different positions of adjustment against the action of its retracting spring.

7. In a surgical instrument of the character described, a handle having a tubular head, a sleeve angularly adjustable in the head, means for clamping the sleeve in different positions of adjustment, a jaw mounted on the sleeve in fixed relation thereto, a plunger reciprocally movable endwise through the sleeve and provided with a jaw movable into and out of pinching co-action with the first-named jaw, and means for moving the plunger endwise.

8. In a device for removing tonsils, a frame having an opening in one end for receiving the tonsil, means slidable on the frame and co-operating with the wall of the opening for removing the tonsil, co-axial members relatively movable endwise one upon the other for operating the tonsil removing means, and means releasable at will for automatically locking one of said members in its tonsil removing position.

9. In a device for removing tonsils, a frame having an opening in one end for receiving the tonsil, means slidable on the frame and cooperating with the wall of the opening for removing the tonsil, co-axial members relatively movable endwise one upon the other for operating the tonsil removing means, and means including a rack and pawl for holding one of said members in its tonsil-removing position.

10. In a device for removing tonsils, a frame having an opening in one end for receiving the tonsil, means slidable on the frame and cooperating with the wall of the opening for removing the tonsil, co-axial members relatively movable endwise one upon the other for operating the tonsil removing means, and means releasable at will for automatically locking one of said members in its tonsil removing position, said members having operating handles at the opposite end of the frame.

In witness whereof I have hereunto set my hand this 11th day of February, 1925.

OTTO H. OESTERWITZ.